United States Patent [19]

Cipullo

[11] Patent Number: 5,091,591
[45] Date of Patent: Feb. 25, 1992

[54] PROCESS AND COMPOSITION

[75] Inventor: Michael J. Cipullo, Mt. Vernon, Ind.

[73] Assignee: General Electric Company, Mt. Vernon, Ind.

[21] Appl. No.: 611,813

[22] Filed: Nov. 13, 1990

[51] Int. Cl.$^5$ .................. C07C 27/26; C07C 39/12
[52] U.S. Cl. ................... 568/703; 568/722; 568/724; 568/727
[58] Field of Search ............... 568/722, 724, 727, 703, 568/708

[56] References Cited

U.S. PATENT DOCUMENTS

| | | | |
|---|---|---|---|
| 2,714,087 | 7/1955 | Steven et al. | 568/703 |
| 4,160,110 | 7/1979 | Carnahan, Jr. | 568/703 |
| 4,359,590 | 11/1982 | Dachs | 568/703 |
| 4,847,433 | 7/1989 | Kissinger | 568/727 |
| 4,876,395 | 10/1989 | Kissinger | 568/728 |
| 4,894,486 | 1/1990 | Neil et al. | 568/703 |

FOREIGN PATENT DOCUMENTS 717634  10/1954  United Kingdom ............... 568/703

Primary Examiner—Werren B. Lone
Attorney, Agent, or Firm—Martin B. Barancik

[57] ABSTRACT

A process comprising the addition of a degradation inhibiting effective amount of an ammonium, alkali metal, alkaline earth metal or transition metal of oxidation number +2 salt of an aliphatic mono or dicarboxylic acid to a composition comprising a phenol and a bisphenol, the addition occurring prior to a procedure which subjects the bisphenol to substantial heat, said bisphenol produced from an acidic ion exchange resin catalyzed reaction of a phenol and a ketone or aldehyde.

14 Claims, No Drawings

PROCESS AND COMPOSITION

BACKGROUND OF THE INVENTION

The dihydric phenols have achieved significant success in their commercial applications. Dihydric phenols are useful in the commercial manufacture of various polymers including the polyarylates, polyamides, epoxies, polyetherimides, polysulfones and the polycarbonates. Significant attention has been directed to the commercial preparations of the dihydric phenols. For many years it has been well known that the acid catalyzed raction of phenol with specific aldehyde or ketone could prepare the 4,4'-dihydric phenol with specific groups derived from the aldehyde or the ketone connecting the two phenolic rings. In particular when phenol is reacted with acetone, the dihydric phenol 4,4'(hydroxyphenyl)propane-2, hereafter known as bisphenol-A is formed. This has particular utility in polycarbonates, polyarylates and copolyestercarbonates as well as epoxies. In order to make certain polymers, in particular the polycarbonates, the bisphenol-A must be particularly pure, for example, as measured by color. Additionally, the process should be particularly efficient since the dihydric phenol costs contribute substantially to the cost of the final polymer. Therefore much attention has been directed to the recovery of bisphenol-A after preparation. Not only is recovery from the major stream containing primarily bisphenol-A important, but because of the economics involved, various side streams or "purge streams" also contain significant quantities of bisphenol-A and should also be processed in manners which maximize bisphenol-A recovery.

Various catalytic systems for acid catalysis of the reaction between phenol and acetone have been investigated and used commercially. The hydrochloric acid catalyzed process is used in a significant number of commercial facilities. However the corrosion caused by the hydrochloric acid on reactors and pre and post reaction equipment leaves much to be desired as far as economics is concerned. Recently, substantial attention has been placed on using ion exchange resin catalyst systems since they do not have significant acid corrosion problems.

Various tactics have been utilized to maximize the quality and quantity of bisphenol-A recovered from the acidic ion exchange resin catalyzed reaction of phenol and acetone. U.S. Pat. No. 4,847,433 utilizes a carbonate metal oxidation number plus two salts of carbonates, to stabilize the bisphenol-A so that significant quantities of quality bisphenol-A can be recovered from various streams. It was thought that the specific acidic material that was being counteracted by the addition of the carbonate salts were minute quantities of strong acid oligomers which were being leached from the resin catalyst during the processing. It was noted that such carbonate salts should not be recycled to the catalyst system since they would very well bring about eventual neutralization of the catalyst system.

U.S. Pat. No. 4,894,486 specifically states that the presence of metal ions is also thought to have an adverse effect on the color of bisphenols probably by promoting degradation. The British Patent 890432 is then cited to show that various other additives have been employed to inhibit the formation of degradation products of the bisphenols. Thus, alkaline earth phosphates, stannic oxide and oxylate, a mixture of tin powder and tin dioxide, terephthalic and isophthalic acids, oxalic, sebacic and adipic acids and boron or antimony trioxides and their mixtures are taught as useful additives for providing thermal stabilities to bisphenols. Additionally in British Patent 890432 is mentioned the concept of utilizing a neutral or amphoteric compound or compound of weakly acidic character and possibly also possessing the property of forming complexes with metallic ions and ability to react with alkaline reacting impurities in the bisphenols is also mentioned. A further British Patent 1022583 teaches that improved color stability of bisphenols is provided by the incorporation of oxalic, citric or tartaric acids or their alkali metal or ammonium salts during a bisphenol manufacturing process. They may be added with the reactants or after the reaction is complete but before the bisphenol is separated from the reaction mixture. The British patents disclose acidic conditions for preparing bisphenol-A but no mention of acid ion exchange resin catalysis is mentioned.

Recently, U.S. Pat. No. 4,894,486 disclosed the use of the hydroxy acids lactic, malic and glyceric and their ammonium or alkali metal salts as stabilizers for bisphenols. No particular preparation of the bisphenol-A was employed and the only examples utilized the acid per se and measured the APHA color before and after heat treatment.

Weakly basic anion exchange columns have also been utilized to contact bisphenol containing fluids. In U.S. Pat. No. 4,191,843, a weakly basic anion exchange resin is used to contact reactor effluent obtained from an acid ion exchange resin catalyst. Instead of the weakly basic anion exchange resin, strongly acidic ion exchange resin in its salt form can also be used. U.S. Pat. No. 4,766,254, utilizes a weakly basic anion exchange resin to contact the mother liquor of bisphenol-A phenol adduct.

As can be seen from this virtual potpourri of prior art there is very little distinction given to the types of impurities which are being addressed in the manufacturing process of bisphenols, particularly bisphenol-A. The fact that any of acids, salts of acids, or bases can be used indicates that both alkaline and acidic impurities are being removed. Therefore there is no real directing nature to the prior art.

It is now been found that when utilizing an acidic ion exchange resin to catalyze a reaction between a phenol and a ketone to produce a bisphenol, particularly phenol and acetone to produce bisphenol-A, it is very advantageous to contact the desired bisphenol produced prior to significantly elevated temperatures with certain salts of particular weak organic acids. Examples of such temperatures include distillation of phenol or bisphenol as well as the separation of bisphenol from bisphenol phenol adduct. In this manner significant stabilization of the bisphenol, particularly bisphenol-A, is achieved when the bisphenol is subjected to a heat treatment, for example distillation of phenol or bisphenol or separation from its adduct of bisphenol with phenol. Degradation is significantly inhibited as shown by the substantial quantity of bisphenol which is capable of recovery and its enhanced color when the salts of the acid of this invention are in contact therewith.

SUMMARY OF THE INVENTION

In accordance with the invention, there is a process comprising the addition of a degradation inhibiting effective amount of an ammonium, alkali, alkaline earth or transition metal of oxidation number +2 metal salt of an aliphatic mono or dicarboxylic acid, to a composition comprising a phenol and a bisphenol the addition occurring prior to a procedure which subjects the bisphenol to substantial heat, said bisphenol produced from an acidic ion exchange resin catalyzed reaction of a phenol and a ketone or aldehyde.

A further aspect of the invention is a composition comprising phenol and a bisphenol in admixture with a bisphenol degradation inhibiting effective amount of an ammonium, alkali, alkaline earth or transition metal of oxidation number +2 metal salt of an aliphatic mono or dicarboxylic acid.

DETAILED DESCRIPTION OF THE INVENTION

The bisphenol, particularly bisphenol-A, is made by the standard acid catalyzed reaction of a phenol and an aldehyde or ketone. When preparing bisphenol-A, the phenol is phenol and the ketone is acetone. An acidic catalyst is used to increase the efficiency of the reaction. This catalyst system is preferably in the heterogeneous form, that is as an ion exchange resin in its acidic form. The ion exchange resin can be, for example, an Amberlite type resin obtained from Rohm and Haas. This resin has styrenic backbone with pendant $SO_3H$ groups which provide the acidic character to the resin. Usually the styrene is crosslinked with a small quantity of divinyl benzene or other crosslinking chemical. This addition of a crosslinker appears to provide structural strength and rigidity to the catalyst. Other ion exchange resins can also be used although it is preferable to use the styrenic backbone crosslinked with the difunctional monomer and having $SO_3H$ groups pendant from the aromatic nucleus of the styrene moiety. The use of these ion exchange resins can bring about certain problems not typically observed with a homogeneous acidic catalyst system. Increased color generation as well as loss of bisphenol-A during certain heat treatments such as distillation and/or bisphenol-A phenol adduct melting and separation can be found to occur.

The group of compounds which inhibit the degradation of the bisphenol is ammonium, alkali, alkaline earth or transition metal of oxidation number +2 metal salt of an aliphatic mono or dicarboxylic acid.

There are no other functional groups on the carboxylic acid, for example hydroxy, keto, epoxy, thio, amino and the like. With respect to the monocarboxylic acids, the carboxy group is preferably at a terminal position and they are from one to twenty carbon atoms in the molecule, usually an alkyl or alkylene group, preferably alkyl. The carbon of the carboxylic acid group is counted. Examples of such monocarboxylic acids include butyric, caproic, capric, myritic, stearic oleic, linolenic, and the like. Monocarboxylic acids of from two to about fourteen carbon atoms are preferred. Branched chain acids such as isocaproic or β-dimethylvaleric acid can also be employed. Dicarboxylic acids can also be employed. Counting the carboxylic acid carbons, dicarboxylic acids from two to about twenty carbon atoms can be readily employed. Generally from three to about sixteen carbon atoms are preferred. The dicarboxylic acid groups are generally in the terminal positions of the molecule. The compound can be saturated or unsaturated, normal or branched. Examples of dicarboxylic acids include oxalic, succinic, adipic, suberic, sebacic, dodecanedioic, maleic, fumaric and the like. Preferred cations are ammonia, sodium, potassium, calcium, magnesium, and zinc.

A stabiliting effective or degradation effective amount of the compound(s) should be employed. Generally an effective amount of from about 1 to about 1000 ppm based upon the bisphenol present in the stream is effective. Below this quantity, effectiveness is difficult to observe. Above this quantity, no additional beneficial results are generally observed. Preferred quantities are generally from about 10 to about 500.

These salts can be added to the process of preparing the bisphenol prior to any substantial heat treatment for maximum effect. Examples of such heat treatment include distillation, melting the adduct of bisphenol and phenol and like elevated temperature treatments. It is preferable to add the additive at a point in the process wherein any excess, unreacted additive would not be brought back to the strong acid condensation catalyst, for example in a recycle stream. For example, the additive can be added to the stream immediately prior to distillation of the bisphenol or separation of the bisphenol phenol adduct by melting.

Below are examples of the invention. These examples are intended to illustrate and exemplify but not narrow the invention.

EXAMPLES

Bisphenol-A is prepared from the strong acid ion exchange resin catalyzed reaction of acetone and phenol. The bisphenol-A is separated as bisphenol-A phenol adduct. Approximately 250 grams of mother liquor of bisphenol-A phenol adduct was placed in a 500 ml pot. The quantity of bisphenol-A present in the mother liquor was analyzed by high pressure liquid chromotography.

The pot is heated with the reflux condenser off and the phenol is collected over head until the pot temperature rises to 210° C. At that point, the reflux condenser water flow is initiated and the solution is allowed to reflux for four hours. A nitrogen blanket was not used to allow air/oxygen contact during the test.

At the end of four hours, the pot residue is again analyzed by high pressure liquid chromatography to determine the weight of bisphenol-A remaining. This is the control.

The same procedure is carried out as above; however 500 ppm of additive based upon the weight of the solution, was added to the pot together with the mother liquor. The final quantity of bisphenol-A was reported after four hours of refluxing. Below are the results reported as percent loss of BPA from the initial quantity. 0% loss is total inhibition of degradation.

| Additive | % Loss Control | % Loss Experimental |
| --- | --- | --- |
| ammonium oxalate | 36.3 | 0 |
| calcium stearate | 6.9 | 0 |
| magnesium stearate | 18.2 | 0 |
| sodium acetate | 36.1 | 23.3 |
| sodium malonate | 19.5 | 0.3 |
| sodium stearate | 26 | 6.9 |
| zinc neodecanate | 13.4 | 0.3 |
| sodium succinate | 37 | 0 |
| titanium stearate | 28 | 23.3 |
| zinc stearate | 7 | 0 |

From these data, it is clear that all the salts of the weak carboxylic acid inhibited the degradation of the bisphenol-A to a greater or lesser extent. Interestingly the type of cation present influences the behavior of the salt substantially as shown in the case of the stearates. Preferred salts from these data are sodium succinate, sodium malonate, ammounium oxalate, magnesium stearate, calcium stearate, sodium gluconate, and zinc stearate. Particularly preferred salts are the ammonium and sodium salts of the dicarboxylic acids, particularly oxalic, malonic, and succinic.

What is claimed is:

1. A process comprising the addition of a degradation inhibiting effective amount of an ammonium, alkali metal, alkaline earth metal zinc of oxidation number +2 salt of an aliphatic mono or dicarboxylic acid having no other functional groups and from two to about eighteen carbon atoms, inclusive, to a composition comprising phenol and bisphenol-A, the addition occurring prior to a procedure which subjects the bisphenol to substantial heat, said bisphenol produced from an acidic ion exchange resin catalyzed reaction of phenol and acetone ketone or aldehyde.

2. A process in accordance with claim 2 wherein the salt is a salt of a monocarboxylic acid.

3. A process in accordance with claim 2 wherein the salt is a salt of a dicarboxylic acid.

4. A process in accordance with claim 1 wherein the salt is present in from about 1 to about 1000 ppm, as measured by amount of bisphenol-A.

5. The process in accordance with claim 4 wherein the salt is a malonate, succinate or stearate.

6. The process in accordance with claim 6 wherein the metallic portion the salt is sodium or ammonium.

7. The process in accordance with claim 6 wherein the salt is sodium succinate.

8. A composition comprising phenol and bisphenol-A in admixture with a bisphenol-A degradation inhibiting effective amount of an ammonium, alkali, alkaline earth or zinc metal of oxidation number +2 metal salt of an aliphatic mono or dicarboxylic acid having no other functional groups and from two to about eighteen carbon atoms, inclusive.

9. The composition in accordance with claim 8 wherein the salt is a salt of a monocarboxylic acid.

10. The composition in accordance with claim 8 wherein the salt is a salt of a dicarboxylic acid.

11. The composition in accordance with claim 8 wherein the salt is present in from about 1 to about 1000 ppm, as measured by bisphenol-A.

12. The composition in accordance with claim 11 wherein the salt is a malonate, succinate or stearate.

13. The composition in accordance with claim 12 wherein, the metallic portion of salt is sodium or ammonium.

14. The composition in accordance with claim 13 wherein the salt is sodium succinate.

* * * * *